Figure 1:
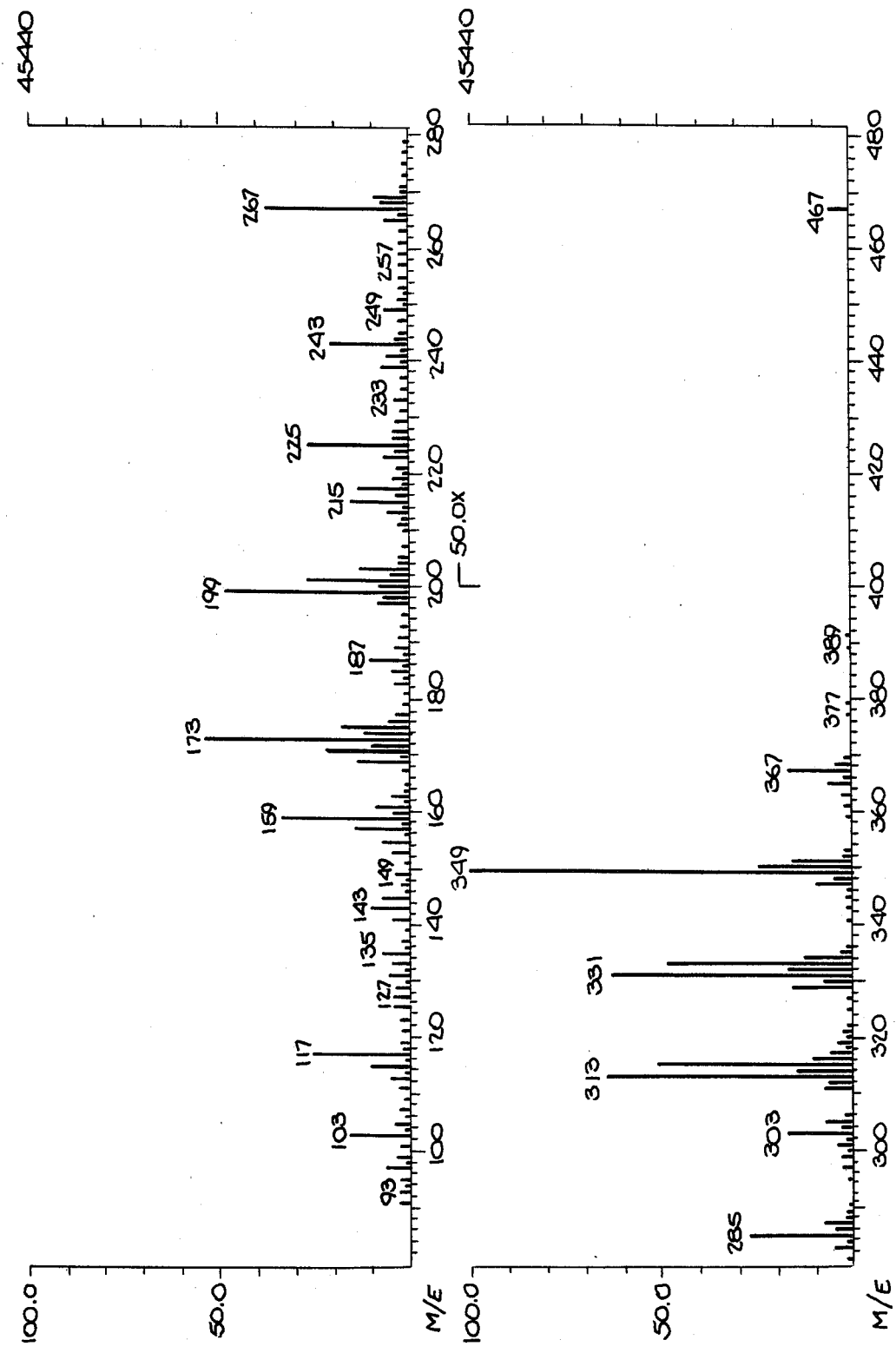

United States Patent [19]

Lam

[11] 4,387,242
[45] Jun. 7, 1983

[54] HYPOCHOLESTEROLEMIC FERMENTATION PRODUCTS AND PROCESS OF PREPARATION

[75] Inventor: Tony Y. K. Lam, Edison, N.J.

[73] Assignee: Merck & Co., Inc., Rahway, N.J.

[21] Appl. No.: 295,189

[22] Filed: Aug. 21, 1981

[51] Int. Cl.³ .................. C07D 309/30; C07C 69/732; C07C 59/46
[52] U.S. Cl. .................. 560/119; 562/501; 549/292
[58] Field of Search ............ 260/343.5; 560/119; 562/501; 549/292

[56] References Cited

U.S. PATENT DOCUMENTS

| | | | |
|---|---|---|---|
| 3,983,140 | 9/1976 | Endo et al. | 260/343.5 |
| 4,137,322 | 1/1979 | Endo et al. | 560/119 |
| 4,231,938 | 11/1980 | Monaghan et al. | 260/343.5 |
| 4,294,846 | 10/1981 | Albers-Schonberg et al. | 260/343.5 |

OTHER PUBLICATIONS

Brown, et al., J. Chem. Soc., Perkin I, 1165–1169, (1976).

*Primary Examiner*—Norma S. Milestone
*Attorney, Agent, or Firm*—William H. Nicholson; Mario A. Monaco

[57] ABSTRACT

Substances isolated after cultivation of a microorganism belonging to the genus Aspergillus in a culture medium include a compound with structural formula:

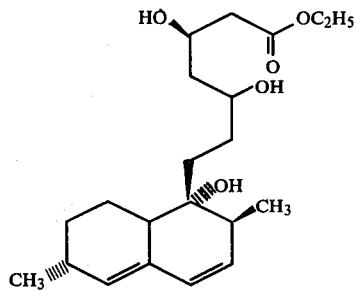

Together with the corresponding free acid of the above ester, its salts and lactone, compound I is a member of a class of hypocholesterolemic and hypolipemic medicaments.

3 Claims, 2 Drawing Figures

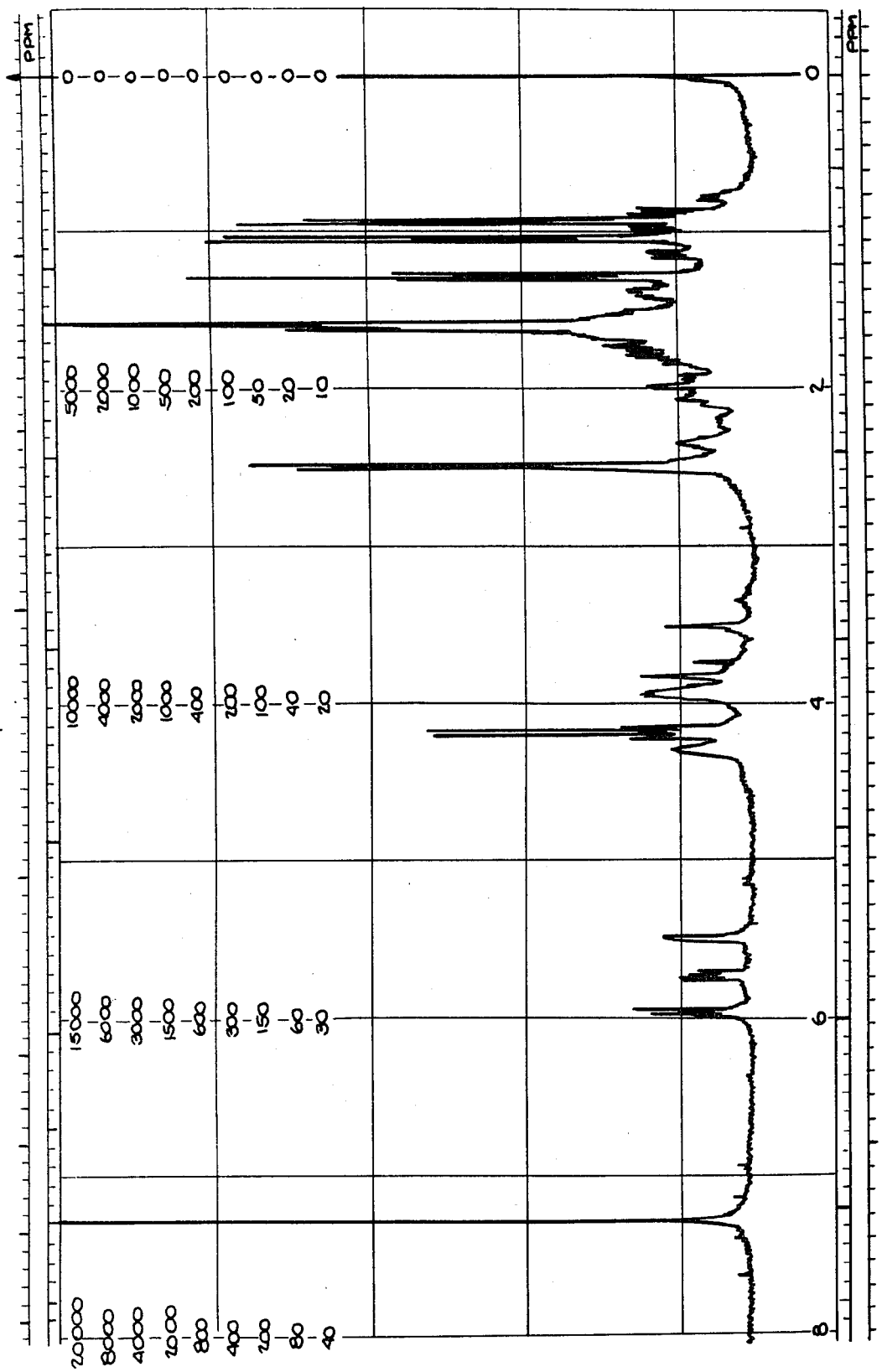

HYPOCHOLESTEROLEMIC FERMENTATION PRODUCTS AND PROCESS OF PREPARATION

SUMMARY OF THE INVENTION

This invention relates to hypocholesterolemic and hypolipemic products from the cultivation of a microfungus of the species Aspergillus. More specifically, it relates to compounds of formulae I, II and III each in substantially pure form:

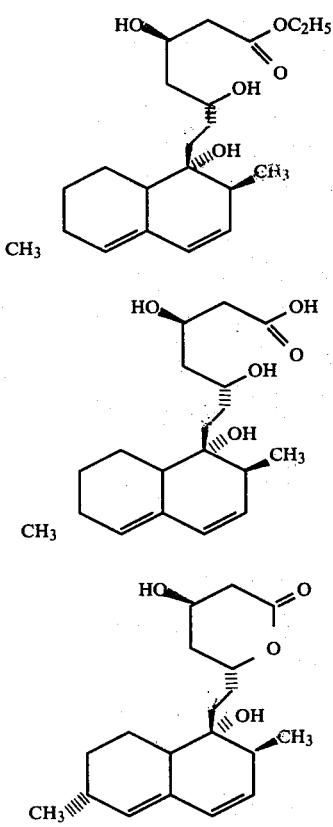

as well as pharmaceutically acceptable salts and esters of compound II. The invention also relates to a process of cultivating the microfungus and isolating from the medium hypocholesterolemic compounds of the above structures. These new compounds have the property of inhibiting cholesterol biosynthesis and are useful against hypercholesterolemia and hyperlipemia.

BACKGROUND OF THE INVENTION

Because of the possible connection between high blood cholesterol and atherosclerosis, many efforts have been made to find ways and substances to reduce serum cholesterol in the mammalian body. One way is to inhibit in mammals the body's ability to synthesize cholesterol.

U.S. Pat. No. 4,231,938 and E.P. publication 0022478 describe the fermentative production of mevinolin and dihydromervinolin, with chemical structures closely related to the novel compounds of this invention, by cultivation of *Aspergillus terreus* in a nutrient medium. Those compounds are highly active anti-hypercholesterolemic agents.

DESCRIPTION OF THE INVENTION

It now has been found that the cultivation of the same microorganism, the microfungus *Aspergillus terreus*, produces an additional substance isolated from the fermentation broth as the ester of Structure I, that is also an inhibitor of the biosynthesis of cholesterol in mammals. The invention also relates to II, pharmaceutically acceptable salts of II and to $C_{1-3}$ alkyl esters of II, and to substituted $C_{1-3}$ alkyl esters of II wherein the substitutent is phenyl, dimethylamino, or acetylamino.

The pharmaceutically acceptable salts of this invention include those formed from cations such as sodium, potassium, aluminum, calcium, lithium, magnesium, zinc, ammonia, ethylenediamine, N-methylglucamine, lysine, arginine, ornithine, choline, N,N'-dibenzylethylene-diamine, chloroprocaine, diethanolamine, procaine, N-benzylphenethylamine, 1-p-chlorobenzyl-2-pyrrolidin-1'-yl-methylbenzimidazole, diethylamine, piperazine, tris(hydroxymethyl)aminomethane, and tetramethylammonium.

The compounds of this invention are useful as antihypercholesterolemic agents for the treatment of artherosclerosis, hyperlipemia and like diseases in humans. They may be administered orally or parenterally in the form of a capsule, a tablet, an injectable preparation or the like. It is usually desirable to use the oral route. Doses may be varied, depending on the age, severity, body weight and other conditions of human patients but daily dosage for adults is within a range of from about 2 mg. to 2000 mg. (preferably 2 to 100 mg) which may be given in two to four divided doses. Higher doses may be favorably employed as required.

The compounds of this invention also have useful antifungal activities. For example, they may be used to control strains of Penicillium sp., *Aspergillus niger*, Cladosporium sp., *Cochliobolus miyabeanus* and *Helminthosporium cynodnotis*. For those utilities they are admixed with suitable formulating agents, powders, emulsifying agents or solvents such as aqueous ethanol and sprayed or dusted on the plants to be protected.

In another aspect of this invention, it relates to a process for producing the compounds of this invention which comprises cultivating a microorganism belonging to the genus Aspergillus and then recovering compound I of this invention from the cultured broth followed by conversion to compound II and/or III. As described in U.S. Pat. No. 4,231,938, the Aspergillus, isolated and identified as a hitherto undescribed microorganism, was designated MF-4833 in the culture collection of Merck and Co., Inc., Rahway, N.J. and a culture thereof was placed on permanent deposit with the American Type Culture Collection, 12301 Parklawn Dr., Rockville, Md. 20852, and has been assigned accession number ATCC 20541. Another isolate, of the organism, designated MF-4845 in the Merck culture collection, has likewise been placed on deposit and has been given the accession number ATCC 20542. Although the use of these is described in connection with the process of this invention, other organisms of the genus Aspergillus including mutants of the above named are also capable of producing these novel compounds and their use is contemplated in carrying out the process of this invention.

The morphological characteristics of the microorganisms MF-4833 and MF-4845 have been found to be those of the genus Aspergillus. Using the criteria specified in the standard authority "Manual of the Aspergilli," Charles Thom and Kenneth B. Rasper, published by the Williams and Wilkins Company, Baltimore, Md., 1945, and by comparison with known species, it has been determined that both strains are *Aspergillus terreus.*

The culture of these organisms to produce the novel compounds is carried out in aqueous media such as those employed for the production of other fermentation products. Such media contain sources of carbon, nitrogen and inorganic salts assimilable by the microorganism.

In general, carbohydrates such as sugars, for example, glucose, fructose, maltose, sucrose, xylose, mannitol and the like and starches such as grains, for example, oats, ryes, cornstarch, corn meal and the like can be used either alone or in combination as sources of assimilable carbon in the nutrient medium. The exact quantity of the carbohydrate source or sources utilized in the medium depends in part upon the other ingredients of the medium but, in general, the amount of carbohydrates usually varies between about 1% and 6% by weight of the medium. These carbon sources can be used individually, or several such carbon sources may be combined in the medium. In general, many proteinaceous materials may be used as nitrogen sources in the fermentation process. Suitable nitrogen sources include for example, yeast hydrolysates, primary yeast, soybean meal, cottonseed fluor, hydrolysates of casein, corn steep liquor, distiller's solubles or tomato paste and the like. The sources of nitrogen either alone or in combination, are used in amounts ranging from about 0.2% to 6% by weight of the aqueous medium.

Among the nutrient inorganic salts which can be incorporated in the culture media are the customary salts capable of yielding sodium, potassium, ammonium, calcium, phosphate, sulfate, chloride, carbonate, and like ions. Also included are trace metals such as cobalt, manganese, iron and magnesium.

It should be noted that the media described in the Examples are merely illustrative of the wide variety of media which may be employed, and are not intended to be limitative. Specifically, the carbon sources used in the culture media to produce the novel compounds of this invention included dextrose, dextrin, oat flour, oatmeal, molasses, citrate, soybean, oil, glycerol, malt extract, cod liver oil, starch, ethanol, figs, sodium ascorbate and lard oil. Included as nitrogen sources were peptonized milk, autolyzed yeast, yeast RNA, tomato paste, casein, primary yeast, peanut meal, distillers solubles, corn steep liquor, soybean meal, corn meal, NZ amine, beef extract, asparagine, cottonseed meal and ammonium sulfate. The major ionic components were $CaCo_3$, $KH_2PO_4$, $MgSO_4.7H_2O$ and $NaCl$ and small amounts of $CaCl_2.6H_2O$ and traces of Fe, Mn, Mo, B and Cu were also present.

The fermentation is carried out at temperatures ranging from about 20° to 37° C.; however, for optimum results it is preferable to conduct the fermentation at temperatures of from about 22° to 30° C. The pH of the nutrient media suitable for growing the Aspergillus culture and producing the novel compounds can vary from about 6.0 to 8.0.

Although the novel compounds are produced by both surface and submerged culture, it is preferred to carry out the fermentation in the submerged state. A small scale fermentation is conveniently carried out by inoculating a suitable nutrient medium with the Aspergillus culture and, after transfer to a production medium, permitting the fermentation to proceed at constant temperature of about 28° C. on a shaker for several days.

The fermentation is initiated in a sterilized flask of medium via one or more stages of seed development. The nutrient medium for the seed stage may be any suitable combination of carbon and nitrogen sources. The seed flask is shaken in a constant temperature chamber at about 28° C. for 2 days, or until growth is satisfactory, and some of the resulting growth is used to inoculate either a second stage seed or the production medium. Intermediate stage seed flasks, when used, are developed in essentially the same manner, that is, part of the contents of the flask from the last seed stage are used to inoculate the production medium. The inoculated flasks are shaken at a constant temperature for several days, and at the end of the incubation period the contents of the flasks are centrifuged or filtered.

For large scale work, it is preferable to conduct the fermentation in suitable tanks provided with an agitator and a means of aerating the fermentation medium. According to this method, the nutrient medium is made up in the tank and sterilized by heating at temperatures of up to about 120° C. Upon cooling, the sterilized medium is inoculated with a previously grown seed of the producing culture, and the fermentation is permitted to proceed for a period of time as, for example, from 3 to 5 days while agitating and/or aerating the nutrient medium and maintaining the temperature at about 28° C. This method of producing the novel compounds is particularly suited for the preparation of large quantities.

Compound I is conveniently isolated from the fermentation broth.

Compound I can be saponified with bases such as NaOH to yield the salts such as the sodium salt of Compound II. Careful acidification of these salts affords the hydroxy acid II which can be converted to other pharmaceutically acceptable salts. The hydroxy acid II or its ammonium salt can be converted to Compound III by refluxing in toluene. Treating Compound I or II under acidic or basic catalysis with methanol, ethanol, propanol, or butanol or with phenyl-, dimethylamino-, or acetylamino-alkanols yield the corresponding esters of Compound II which also form a part of this invention.

The physico-chemical properties of Compound I are summarized as follows:

1. Molecular Formula: $C_{21}H_{34}O_5$
2. Mass Spectrum: The mass spectrum was recorded using the chemical ionization technique and displayed in FIG. 1. The peak m/z=367 corresponds to M+1.
3. $^1$H NMR Spectrum: The spectrum was recorded in $CDCl_3$ solution and chemical shifts are shown in FIG. 2 in ppm relative to internal tetramethylsilane at zero ppm.

On the basis of these and other data, the structure of Compound I is believed, with a considerable degree of certainty, to have the chemical structure I:

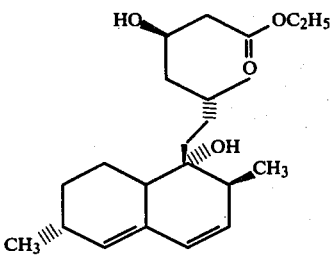

I

The corresponding hydroxy acid, Compound II, and lactone, Compound III then, have the structures:

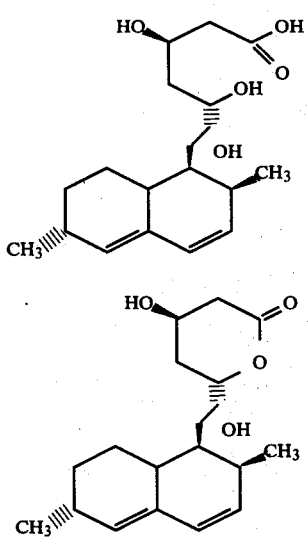

II

III

EXAMPLE 1

Preparation of Compound I

A. Fermentation

The medium used in each step of the fermentation comprised:
  Corn steep liquor: 5 g
  Tomato paste: 40 g
  Oat Flour: 10 g
  Glucose: 10 g
  Trace element solution: 10 ml
  Distilled water: 1000 ml
adjusted to pH 6.8 with sodium hydroxide.
  The trace element solution comprised:
  $FeSO_4.7H_2O$: 1 g
  $MnSO_4.4H_2O$: 1 g
  $CuCl_2.2H_2O$: 25 mg
  $CaCl_2$: 100 mg
  $H_3BO_4$: 56 mg
  $(NH_4)_6Mo_7O_{24}.4H_2O$: 19 mg
  $ZnSO_4.7H_2O$: 200 mg
  distilled water: 1 liter
All media were checked for sterility before inoculation with a microorganism.

To a 250 ml non-baffled Erlenmeyer flask was charged 40 ml of medium and the contents of one tube of lyophillized organism MF 4833. It was then shaken for 24 hours at 28° C. on a rotary shaker at 220 rpm. New flasks were then charged with 40 ml of medium and 1 ml of the first flasks's contents and were shaken an additional 24 hours at 28° C. A 2 liter flask was then charged with 400 ml of medium and 10 ml of the second stage fermentation mixture and this too was shaken for 24 hours at 28° C.

A 200 gallon stainless steel fermentation vat was then charged with 501 liters of a medium comprising.
  lactose: 2% wt/vol
  distiller solubles: 1.5% wt/vol
  autolyzed yeast: 0.5% wt/vol
  Polyglycol P2000: 0.25% wt/vol
whose pH was adjusted to 7.0. This was sterilized 15 minutes at 121° C. One liter of the third stage above was then charged and the mixture was incubated at 130 rpm at 28° C. for 96 hours with an air flow of 10 cfm.

B. Isolation

About 37.5 lbs. (¾ bag) of a silicaceous filter aid was added to 110 gal. whole broth from the culture of MF-4833 described above and the mixture was filtered through an 18-inch filter press. The clarified filtrate, (pH 6.6) was adjusted to pH 4.0 by careful addition of 450 ml of concentrated hydrochloric acid, and extracted by agitation with about one-third volume (36 gal.) of ethyl acetate. After separation, the upper solvent layer was removed, and the water phase again extracted with ethyl acetate (38 gal.) in a similar fashion. After separation, the two extracts were combined and back-washed by agitation with about twelve gallons of water. After separation, the ethyl acetate solution was concentrated under vacuum at a temperature below 30° C., first in a stirred kettle, and finally in a rotary vacuum evaporator to a residual volume of slightly less than one gallon.

Approximately 1 gal. (3800 ml) of ethyl acetate concentrate from the preceding extraction was further concentrated in a rotary evaporator (ca 10 mm, 40° C. bath) to a syrup and was then concentrated twice more, after addition of about one liter of methylene chloride in two portions, to free the syrup of polar solvent. The final oil of about 300 ml which contained about 250 g of solids by dry weight determination, was made up to about 750 ml with ethyl acetate:methylene chloride (30/70; v/v) and 200 g of silica gel was added and mixed in to form a slurry. This was layered over the top of a 14 cm by 36 cm column bed holding 2.5 kg of the same silica gel, in about 7.5 L volume, which had been packed as a slurry in the same solvent mixture. Development with the same solvent was continued until 3 liters of effluent was taken off as forerun.

Development with ethyl acetate-methylene chloride (50/50; v/v) was begun, taking 800 ml effluent fractions. Twelve fractions were taken, then 100% ethyl acetate elution was begun, and after seven more fractions, 100% acetone elution was begun. Peak activity was found in fraction 8. It was concentrated to an oil for further purification; dry wt. by solids determination was 9.0 gm.

Fraction 8 from the silica gel column was triturated with 50 ml methylene chloride and filtered; the dried filter cake weighed 4.9 gm. The filtrate was charged to a 2-inch I.D. by 1-meter long column filled with Sephadex LH-20 dextran gel (Pharmacia) swollen and equilibrated in methylene chloride, and the column was eluted with methylene chloride at a rate of 15 ml/min. Compound I was eluted between 0.64 and 0.81 column volumes. Solvent was removed from this peak leaving a slightly brown residue weighing approximately 0.290 gm. This residue (213 mg) was taken up in 1.5 ml of CH₂Cl₂-CH₃CN (65–35), charged to a prepacked and equilibrated silica gel column (EM LOBAR Size B) and eluted with CH₂Cl₂—CH₃CN (65/35) at 5 ml/min. Evaporation of solvent from the peak eluting between 235 and 360 ml of eluant left 121 mg of crystalline material, m.p. 155°–160° C.

Eighty-two mg of this material was recrystallized from 0.6 ml of absolute ethanol. 2 L of ethanol mother liquors and wash (containing solids at 46 mg/ml, therefore 92 g solids) was evaporated to an oil under vacuum at 40° C. To remove the last trace of ethanol, the oil was taken up in 1.5 L of toluene and the solvent removed under vacuum. Trituration of the residue in cold toluene (1 L) overnight followed by centrifugation and flash evaporation of the centrifugate yielded an oil. This oil was then taken up in 450 ml of hexanes:toluene:methanol 4:1:1 (solvent A), allowed to stand overnight at room temperature, and then centrifuged. The supernatant (total solid 64.35 g) was then charged onto an 8 L Sephadex LH-20 column (10.2×100 cm) equilibrated in solvent A. Elution was done in the same solvent system. The fractions between elution volumes 10,000 ml–12,000 ml were pooled and solvents removed under vacuum. The residue from two such runs were combined (12.4 g) and redissolved in hexanes:toluene:methanol (solvent B) 3:1:1 and rechromatographed on an LH-20 column (bed vol. 930 ml) in the same solvent system. Eluates between elution volumes 1490 ml–2460 ml were pooled and the solvent removed under vacuum. A CH₂Cl₂ solution of the residue (5.4 g) was then adsorbed onto a silica gel column (E. Merck, silica gel 60, 35–70 mesh, 272 g) and elution was done in a stepwise gradient of MeOH/EtOAc/CH₂Cl₂ and the 200 ml fractions were analyzed by TLC. The fractions from 10% and 25% MeOH/EtOAc elutions were pooled and the solvent stripped. The residue was chromatographed on an ES-chromegabond MC-18 column (0.96×50 cm) using the mobile phase MeCN:H₂O 50:50 at a flow rate of 5 ml/min, monitoring at 260 nm, with the fraction collector set at 0.5 min/tube. Fraction 27 (43 mg) from this HPLC step was further purified by E. Merck analytical 20×20 cm silica gel 60F plates with 2 passes in EtOAc. This procedure yielded two UV bands. The faster-moving one was then purified to homogeneity by HPLC using a similar procedure as before yielding I (2 mg).

EXAMPLE 2

Preparation of Compound II and Its Alkali and Alkaline Earth

To a solution of 36.6 mg of the product of Example 1 in 2 ml of ethanol is added 1 ml of aqueous NaOH ($10^{-4}$ moles; 1 equivalent). After one hour at room temperature, the mixture is taken to dryness in vacuo to yield the sodium salt of Compound II.

In like manner the potassium salt is prepared using one equivalent of potassium hydroxide, and the calcium salt using one equivalent of CaO.

The sodium salt is dissolved in 2 ml of water, cooled in ice and acidified slowly with 0.5 M HCl. The mixture is extracted with methylene chloride, back-extracted with water, dried over MgSO and filtered. The filtrate is concentrated by flash evaporation to yield Compound II.

EXAMPLE 3

Ammonium Salt of Compound II

The sodium salt from Example 2 is dissolved in 2 ml of water, cooled in ice and acidified slowly with 0.5 M HCl. The mixture is extracted with ethyl acetate, back-extracted with water, dried over MgSO₄ and filtered. The filtrate is treated with anhydrous ammonia with stirring and cooling to precipitate the ammonium salt.

EXAMPLE 4

Ethylenediamine Salt of Compound II

To a solution of 0.50 g of the ammonium salt of Compound II in 10 ml of methanol is added 75 μl of ethylenediamine. The methanol is stripped off under vacuum and the residue is triturated with acetone, stored in the cold, and filtered to obtain the ethylenediamine salt of Compound II.

EXAMPLE 5

Tris(hydroxymethyl)aminomethane Salt of Compound II

To a solution of 202 mg of the ammonium salt of Compound II in 5 ml of methanol is added a solution of 60.5 mg of tris(hydroxymethyl)aminomethane in 5 ml of methanol. The solvent is removed in vacuo and the residue triturated with a 1:1 mixture of acetonitrile:methanol. The desired tris(hydroxymethyl)aminomethane salt of Compound II is filtered off and dried.

EXAMPLE 6

L-Lysine Salt of Compound II

A solution of 0.001 mole of L-lysine and 0.0011 mole of the ammonium salt of Compound II in 15 ml of 85% ethanol is concentrated to dryness in vacuo. The residue is triturated with 10 ml of warm ethanol, cooled, and filtered to give the L-lysine salt of Compound II.

Similarly prepared are the L-arginine, L-ornithine, and N-methylglucamine salts of Compound II.

EXAMPLE 7

Tetramethylammonium Salt of Compound II

A mixture of 68 mg of Compound III in 2 ml of methylene chloride and 0.08 ml of 24% tetramethylammonium hydroxide in methanol is diluted with ether to cause precipitation of the tetramethylammonium salt of Compound II.

EXAMPLE 8

Methyl Ester of Compound II

To a solution of 400 mg of the product, Compound I, in 100 ml of absolute methanol is added 10 ml 0.1 M sodium ethoxide in absolute ethanol. This solution is allowed to stand at room temperature for one hour, is then diluted with water and extracted twice with water, the ethyl acetate, dried over anhydrous sodium sulfate, is removed in vacuo to yield the methyl ester of Compound II.

In like manner, by the use of equivalent amounts of propanol, butanol, isobutanol, t-butanol, amylalcohol, isoamylalcohol, 2-dimethylaminoethanol, benzylalcohol, phenethanol, 2-acetamidoethanol, and the like, the corresponding esters are obtained.

What is claimed is:

1. A compound of structural formula:

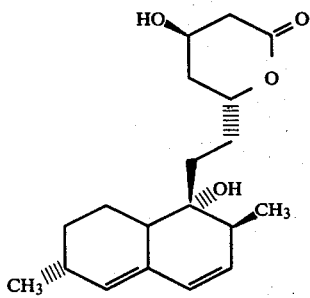

in substantially pure form or the corresponding hydroxy acid II in substantially pure form

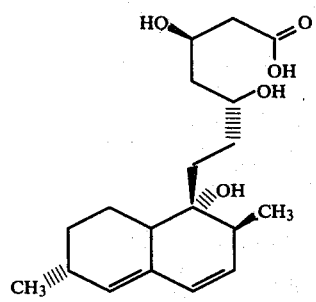

or a pharmaceutically acceptable salt of compound II or a C$_{1-3}$alkyl ester of II, or a substituted C$_{1-3}$alkyl ester of II wherein the substituent is phenyl, dimethylamino, or acetylamino, wherein the salts and esters of II are in substantially pure form.

2. The compound of claim 1 with structural formula:

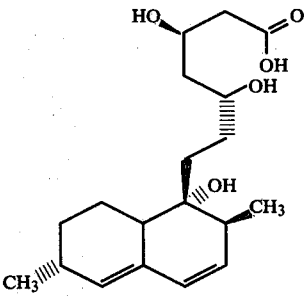

in substantially pure form.

3. The compound of claim 1 with structural formula:

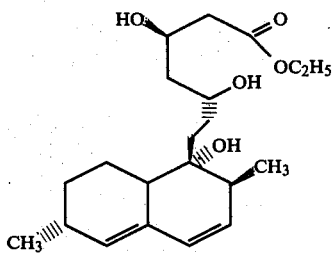

in substantially pure form.

* * * * *